United States Patent [19]

Vorbruggen et al.

[11] Patent Number: 4,983,629
[45] Date of Patent: * Jan. 8, 1991

[54] 11-HALOPROSTANE DERIVATIVES, PROCESSES FOR THEIR PREPARATION AND THEIR USE AS MEDICINAL AGENTS

[75] Inventors: Helmut Vorbruggen; Norbert Schwarz; Olaf Loge; Claus-Steffen Sturzebecher; Walter Elger, all of Berlin, Fed. Rep. of Germany

[73] Assignee: Schering Aktiengesellschaft, Berlin and Bergkamen, Fed. Rep. of Germany

[*] Notice: The portion of the term of this patent subsequent to Sep. 26, 2006 has been disclaimed.

[21] Appl. No.: 369,168

[22] Filed: Jun. 21, 1989

Related U.S. Application Data

[63] Continuation of Ser. No. 929,310, Nov. 12, 1986, Pat. No. 4,870,104, which is a continuation of Ser. No. 717,266, Mar. 8, 1985, abandoned.

[51] Int. Cl.$^5$ .................. C07C 177/00; A61K 31/557
[52] U.S. Cl. .................. 514/530; 514/570; 514/573; 548/131; 548/237; 549/303; 549/374; 560/62; 560/121; 560/231; 562/472; 562/503; 564/93; 564/98; 564/99; 564/152; 564/158; 564/171; 564/189
[58] Field of Search .......... 560/121, 62, 231; 562/472, 503; 568/645, 838, 542, 591; 548/237, 131; 549/363, 374; 564/189, 171, 152, 158, 98, 99, 93; 514/530, 570, 573

[56] References Cited

U.S. PATENT DOCUMENTS 4,870,104  9/1989  Vorbrussen .................. 514/530

Primary Examiner—Robert Gerstl
Attorney, Agent, or Firm—Millen, White & Zelano

[57] ABSTRACT

11-Haloprostane derivatives of general Formula I

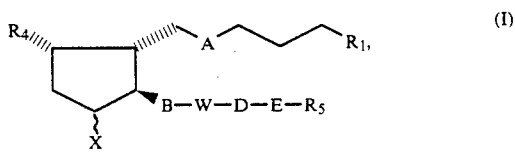

wherein
X is F, Cl or Br,
$R_1$ is the residue $CH_2OH$ or

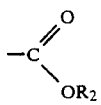

wherein $R_2$ means a hydrogen atom, an alkyl, cycloalkyl, aryl, phenacyl or heterocyclic residue,
A is a —$CH_2$—$CH_2$— or cis—$CH$=$CH$—group,
B is a —$CH_2$—$CH_2$— or trans—$CH$=$CH$— or a —$C$≡$C$—group,
W is an ethylenedioxymethylene group or a hydroxymethylene group,
D and E together mean a direct bond or
D is a $C_{1-10}$-alkylene group,
E is an oxygen or sulfur atom, a direct bond, a —$C$≡$C$—bond or a —$CR_6$=$CR_7$-group with $R_6$ and $R_7$ meaning a hydrogen atom, a chlorine atom or an alkyl group,
$R_4$ is a hydroxy group,
$R_5$ is a hydrogen atom, an alkyl, a cycloalkyl, an aryl or a heterocyclic group, and the salts thereof with physiologically compatible bases, processes for their preparation, and use thereof as agents inhibiting gastric acid secretion.

15 Claims, No Drawings

11-HALOPROSTANE DERIVATIVES, PROCESSES FOR THEIR PREPARATION AND THEIR USE AS MEDICINAL AGENTS

CROSS-REFERENCE TO RELATED APPLICATIONS

This application is a continuation in part of allowed application Ser. No. 06/929,310 filed Nov. 12, 1986, U.S. Pat. No. 4,870,104 which is a continuation of abandoned application Ser. No. 06/717,266, filed Mar. 8, 1985, the National Phase of PCT/DE84/00139 filed July 5, 1984.

BACKGROUND OF THE INVENTION

Prostaglandin $D_2$ is a natural prostaglandin occurring in many organs, but above all in the brain and performing a large number of biological functions. However, prostaglandin $D_2$ as well as analogs of $PGD_2$ (cf. DOS 2,517,773) are even less stable chemically than the prostaglandins of the E series.

Interest has, therefore, existed in developing chemically stable analogs of the prostaglandin D series having the same or a similar biological activity as $PGD_2$. Several chemically stable 11α- and 11β-fluoro- or -chloro-derivatives of 9α,15α-dihydroxy-5-cis-13-trans-prostanoic acid have been described in chemical literature [E. Arroniz et al., Prostaglandins 16:47 (1978)]; however, apart from relatively weak bronchodilatory properties of the 11α-fluoro-derivative, this publication neither discusses biological data nor does it disclose the synthesis of other 11-haloprostanoic acid analogs.

SUMMARY OF THE INVENTION

We have now discovered that 11-fluoro-, 11-chloro- and 11-bromo-derivatives of 9α,15α-dihydroxyprostanoic acid, as well as especially modified analogs of these 11-haloprostanoic acids, which have thus been rendered stable metabolically, possess, surprisingly, interesting biological activities; in this connection the structural modifications aim at prolonging duration of efficacy as well as increasing the selectivity of the biological activities.

The invention relates to 11-haloprostane derivatives of general Formula I

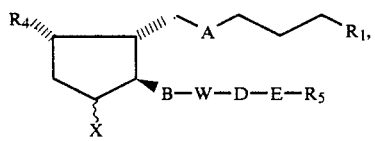

wherein
X is F, Cl or Br,
$R_1$ is the residue $CH_2OH$ or

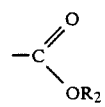

with $R_2$ meaning a hydrogen atom, an alkyl, cycloalkyl, aryl, phenacyl or heterocyclic residue, or
$R_1$ is a

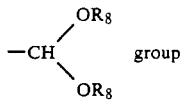 group wherein $R_8$ can be an alkyl group of 1-5 carbon atoms, or
$R_1$ is a

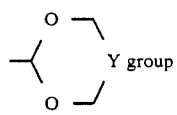 Y group wherein Y can be a direct bond or an alkylene group of 1-5 carbon atoms which is substituted by $C_{1-4}$-alkyl or which is unsubstituted, or $R_1$ is a

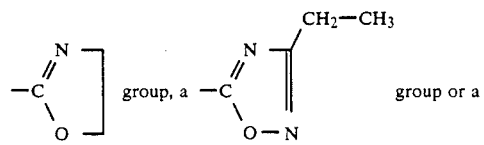

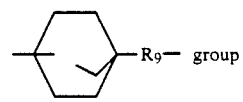 group wherein $R_9$ can be a hydrogen atom or a methyl group, or
$R_1$ is the residue

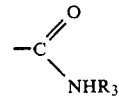

with $R_3$ meaning an acid residue or the residue $R_2$,
A is a $-CH_2-CH_2-$ or cis$-CH=CH-$group,
B is a $-CH_2-CH_2-$ or trans$-CH=CH-$ or $-C\equiv C-$group,
W is an ethylenedioxymethylene group or a free or functionally modified hydroxymethylene group wherein the OH-group can be in the α- or β-position,
D and E together mean a direct bond or
D is a straight-chain or branched-chain alkylene group of 1-10 carbon atoms which can optionally be substituted by fluorine atoms,
E is an oxygen or sulfur atom, a direct bond, a $-C\equiv C-$bond or a $-CR_6=CR_7-$group wherein $R_6$ and $R_7$ are different from each other and mean a hydrogen atom, a chlorine atom or an alkyl group,
$R_4$ is a free or functionally modified hydroxy group,
$R_5$ is a hydrogen atom, an alkyl group, a methoxyalkyl group, a halogen-substituted alkyl, a cycloalkyl, an optionally substituted aryl or a heterocyclic group and if $R_2$ means a hydrogen atom, the salts thereof with physiologically compatible bases.

The halogen atoms in the 11-position of Formula I can be in the α- as well as β-position.

Alkyl groups $R_2$ are considered to be straight or branched alkyl groups of 1-10 carbon atoms, e.g. methyl, ethyl, propyl, butyl, isobutyl, tert-butyl, pentyl, neopentyl, hexyl, heptyl, decyl. The alkyl groups $R_2$ can be optionally mono- to polysubstituted by halogen atoms, alkoxy groups, optionally substituted aryl or aroyl groups, dialkylamino and trialkylammonium; the single substitution is to be preferred. Examples for substituents are fluorine, chlorine or bromine, phenyl, dimethylamino, diethylamino, methoxy, ethoxy. Preferred alkyl groups $R_2$ are those of 1–4 carbon atoms, such as, for example, methyl, ethyl, propyl, dimethylaminopropyl, isobutyl, butyl.

Suitable aryl groups $R_2$ are substituted as well as unsubstituted aryl groups, e.g. phenyl, 1-naphthyl and 2-naphthyl, each of which can be substituted by 1–3 halogen atoms, a phenyl group, 1–3 alkyl groups of 1–4 carbon atoms each, a chloromethyl, fluoromethyl, trifluoromethyl, carboxy, hydroxy or alkoxy group of 1–4 carbon atoms. Preferred are the substituents in the 3- and 4-positions on the phenyl ring, e.g. fluorine, chlorine, alkoxy or trifluoromethyl in the 3-position, or hydroxy in the 4-position.

The cycloalkyl group $R_2$ can contain in the ring 3–10, preferably 5 and 6 carbon atoms. The rings can be substituted by alkyl groups of 1–4 carbon atoms. Examples are cyclopentyl, cyclohexyl, methylcyclohexyl and adamantyl.

Suitable heterocyclic groups $R_2$ are 5- and 6-membered heterocycles containing at least one hetero atom, preferably nitrogen, oxygen or sulfur. Examples are 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, 2-tetrazolyl, and others.

Suitable as the acid residue $R_3$ are physiologically compatible acid residues. Preferred acids are organic carboxylic acids and sulfonic acids of 1–15 carbon atoms pertaining to the aliphatic, cycloaliphatic, aromatic, aromatic-aliphatic and heterocyclic series. These acids can be saturated, unsaturated and/or polybasic and/or substituted in the usual way. Examples for substituents are alkyl, hydroxy, alkoxy, oxo or amino groups or halogen atoms. The following carboxylic acids can be cited as examples: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, benzoic acids substituted by halogen, trifluoromethyl, hydroxy, alkoxy or carboxy groups, nicotinic acid, isonicotinic acid, furan-2-carboxylic acid, cyclopentylpropionic acid. Especially preferred acyl residues are considered to be those of up to 10 carbon atoms. Examples for sulfonic acids are methanesulfonic acid, ethanesulfonic acid, isopropanesulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(β-chloroethyl)aminosulfonic acid, N,N-diisobutylaminosulfonic acid, N,N-dibutylaminosulfonic acid, pyrrolidino-, piperidino-, piperazino-, N-methylpiperazino and morpholinosulfonic acids.

The keto and hydroxy groups in W and $R_4$ can be functionally modified, for example by etherification, esterification as well as ketalizing, wherein also the modified hydroxy group in W can be in the α- or β-position.

Ether and acyl residues are those residues known to persons skilled in the art. Readily cleavable ether residues are preferred, such as, for example, the tetrahydropyranyl, tetrahydrofuranyl, α-ethoxyethyl, trimethylsilyl, dimethylsilyl, tert-butylsilyl and tribenzylsilyl residues. Acyl residues can be the same as mentioned for $R_3$; worth citing by name are, for example, acetyl, propionyl, butyryl and benzoyl.

Alkyl groups $R_5$ can be straight-chain and branched-chain, saturated and unsaturated alkyl residues, preferably saturated ones, of 1–10, especially 1–6 carbon atoms which can be substituted, if desired, by optionally substituted aryl. Examples are methyl, ethyl, propyl, butyl, isobutyl, tert-butyl, pentyl, hexyl, heptyl, octyl, butenyl, isobutenyl, propenyl, pentenyl, benzyl, m- and p-chlorobenzyl groups.

If the alkyl groups $R_5$ are halogen substituted, suitable halogens are fluorine, chlorine and bromine.

The cycloalkyl group $R_5$ can contain in the ring 3–10, preferably 3–6 carbon atoms. The rings can be substituted by alkyl groups of 1–4 carbon atoms. Examples are cyclopropyl, cyclobutyl, cyclopentyl, cyclohexyl, methylcyclohexyl and adamantyl.

Examples for substituted and unsubstituted aryl groups $R_5$, respectively, are: phenyl, 1-naphthyl and 2-naphthyl, each of which can be substituted by 1–3 halogen atoms, a phenyl group, 1–3 alkyl groups of 1–4 carbon atoms each, a chloromethyl, fluoromethyl, trifluoromethyl, carboxy, alkoxy or hydroxy group. Preferred is the substitution in the 3- and 4-positions on the phenyl ring, for example by fluorine, chlorine, alkoxy or trifluoromethyl, or in the 4-position by hydroxy.

Suitable heterocyclic groups $R_5$ are 5- and 6-membered heterocycles containing at least one hetero atom, preferably nitrogen, oxygen or sulfur. Examples are 2-furyl, 2-thienyl, 2-pyridyl, 3-pyridyl, 4-pyridyl,. oxazolyl, thiazolyl, pyrimidinyl, pyridazinyl, pyrazinyl, 3-furyl, 3-thienyl, and others.

Suitable as the alkylene group D are straight-chain or branched-chain, saturated and unsaturated alkylene residues, preferably saturated ones of 1–10, especially 1–5 carbon atoms, which can optionally be substituted by fluorine atoms. Examples are: methylene, fluoromethylene, difluoromethylene, ethylene, 1,2-propylene, ethylethylene, trimethylene, tetramethylene, pentamethylene, 1,1-difluoroethylene, 1-fluoroethylene, 1-methyltetramethylene, 1-methyltrimethylene, 1-methylenethylene, 1-methylenetetramethylene.

Suitable for salt formation are inorganic and organic bases as known to persons skilled in the art for forming physiologically compatible salts. Examples are alkali hydroxides, such as sodium and potassium hydroxide, alkaline earth hydroxides, such as calcium hydroxide, ammonia, amines, such as ethanolamine, diethanolamine, triethanolamine, N-methylglucamine, morpholine, tris(hydroxymethyl)methylamine, etc.

Preferably, x is Cl or F, more preferably, in α-configuration, and $R_5$ is cycloalkyl, more preferably cyclopentyl. Preferably, $R_1$ is

R$_2$ is H, A is cis—CH=CH—, R$_4$ is —OR, R is H, B is trans—CH=CH— and W is CH$_2$OR. (5Z,13E)-9α-15α-dihydroxy-11α-fluoro-15-cyclohexyl-16,17,18,19,20-pentanor-5,13-prostadienoic acid and (5Z,13E)-9α-15α-dihydroxy-11α-chloro-15-cyclohexyl-16,17,18,19,20-pentanor-5,13-prostadienoic acid are particularly preferred. These compounds, in particular, exhibit increased inhibition of platelet aggregation in mammals and increased affinity toward the PGD$_2$ receptor.

The invention furthermore relates to processes for preparing the 11-haloprostane derivatives of general Formula I according to this invention, characterized in that, in a manner known per se, a compound of general Formula II

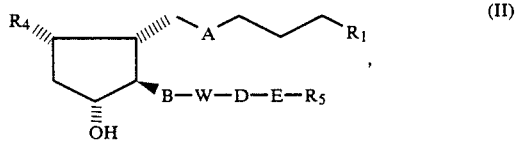

wherein R$_1$ means the residues

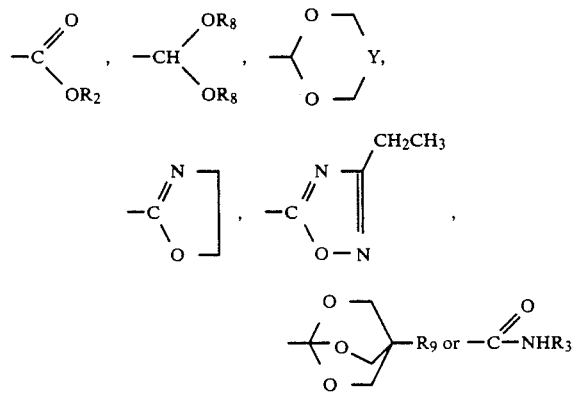

with the above-indicated meanings and A, B, D, E, R$_2$, R$_3$ and R$_5$ have the above-given meanings and free OH-groups in R$_4$ and W are optionally blocked, (a) is directly converted into the corresponding 11β-chloro or 11β-bromo derivatives with triphenylphosphine/CCl$_4$, C$_2$Cl$_6$, CBr$_2$Cl$_4$ or CBr$_4$, (b) is reacted to the corresponding 11β-halogen compounds by reaction with an optionally halogenated alkyl or arylsulfonic acid chloride or anhydride and by subsequent reaction with a halogenide, or (c) is converted into the corresponding 11β-tosyloxy derivatives with diethylazodicarboxylate/triphenylphosphine/zinc tosylate in tetrahydrofuran, and these derivatives are reacted with fluoride, chloride or bromide salts to the corresponding 11α- haloprostanoic acid derivatives and optionally subsequently the blocking groups present are split off. [Cf. W. C. Still et al., Tetrahedron Letters, 4461 (1982).]

Reaction of II with triphenylphosphine/CCl$_4$, C$_2$Cl$_6$, CBr$_4$ or C$_2$Br$_2$Cl$_4$ takes place conventionally, for example in absolute acetonitrile or pyridine as the solvent. On account of the large volume requirement of the thus-formed O-triphenylphosphonium salts, the less hindered 11α-hydroxy group will be reacted first selectively in 9α,11α-diols. Selective blockage of the 15α-hydroxy group is accomplished by acylation of the phenylboric acid esters of the 9α,11α-hydroxy groups in 9α,11α,15α-trihydroxyprostanoic acid esters.

If substituents requiring volume, such as methyl groups, are in the 15- or especially in the 16-position, then blockage of the 15-hydroxy group is likewise superfluous since selectively only the 11α-hydroxy group will react first with triphenylphosphine/CCl$_4$, C$_2$Cl$_6$, CBr$_4$ and C$_2$Br$_2$Cl$_4$, respectively. This also holds true with a certain limitation for the reaction of compounds of general Formula II with triphenylphosphine/azo ester/Zn tosylate, as well as with activated sulfonic acid derivatives. These reactions are conventionally conducted in an optionally halogenated alkyl- or arylsulfonic acid chloride or anhydride in the presence of an amine, e.g. pyridine, 4-dimethylaminopyridine or triethylamine at temperatures of between −20° and +100° C. The nucleophilic substitution of the 11α- or 11β-sulfonates with an ionic halogenide, such as preferably tetrabutylammonium fluoride, CsF, tetrabutylammonium chloride, LiCl, LiBr or tetrabutylammonium bromide, takes place in an inert solvent, e.g. dimethylformamide, acetonitrile, hexamethylphosphoric triamide, tetrahydrofuran, at temperatures of between 0° and 80° C.

For the synthesis of 9α-acyloxy or 9α,15α-diacyloxy derivatives wherein one or both hydroxy groups are selectively blocked, the top chain is suitably first of all synthesized, starting with an 11α-tetrahydropyranyl-13-tert-butyldimethylsilyl ether Corey lactone according to DOS 3,107,100 by means of DIBAL-H reduction, Wittig reduction, CH$_2$N$_2$ esterification and O-benzoylation of the 9-hydroxy group. Splitting off of the silyl group with a fluoride, oxidation of the 13-alcohol to the 13-aldehyde, as well as Wittig reaction with substituted Horner-Wittig reagents then lead to construction of the lower chain. Finally, reduction of the 15-keto group with NaBH$_4$ and subsequent separation of epimers yield the 9α-benzoylated 11α-tetrahydropyranyl(THP)-15α-alcohol.

In case of substituents in the 16-position, e.g. the 16,16-dimethyl analogs, the 11α-THP-group is then split off with acetic acid-H$_2$O-THF, and the 9α-benzoyloxy-11α,15α-dihydroxy-16,16-dimethylprostanoic acid methyl ester is reacted directly with triphenylphosphine-azo ester-zinc tosylate to obtain the 9α-benzoyloxy-11β-tosyloxy-15α-hydroxy-16,16-dimethylprostanoic acid methyl ester.

If the 15α-hydroxy group is relatively unhindered, this hydroxy group must likewise be benzoylated to the 9α,15α-dibenzoyloxy-11α-THP-prostanoic acid methyl ester before the 11α-THP-group is split off selectively and can then be reacted to the corresponding 11β-halogen or 11β-tosyloxy derivatives.

The reduction to the compounds of general Formula I wherein R$_1$ means a —CHO or —CH$_2$OH group is conducted in a reducing agent suitable for reducing esters or carboxylic acids, such as diisobutyl aluminum hydride or lithium aluminum hydride. Suitable solvents are diethyl ether, tetrahydrofuran, dimethoxyethane, toluene, etc. The reaction temperature ranges from −30° to the boiling point of the solvent employed, preferably from 0° to 30° C.

Liberation of the functionally modified hydroxy groups takes place according to conventional methods.

For example, the splitting off of hydroxy blocking groups, e.g. the tetrahydropyranyl residue, is effected in an aqueous solution of an organic acid, e.g. oxalic acid, acetic acid, propionic acid, etc., or in an aqueous solution of an inorganic acid, such as, for example, hydrochloric acid. To improve solubility, a water-miscible, inert organic solvent is suitably added. Organic solvents that can be used are, for example, alcohols, such as methanol and ethanol, and ethers, such as dimethoxyethane, dioxane and tetrahydrofuran. Tetrahydrofuran is employed with preference. The splitting-off step is preferably conducted at temperatures of between 20° and 80° C.

Saponification of the acyl groups takes place, for example, with alkali or alkaline earth carbonates or hydroxides in an alcohol or in the aqueous solution of an alcohol. Aliphatic alcohols can be utilized as the alcohols, e.g. methanol, ethanol, butanol, etc., preferably methanol. Suitable alkali carbonates and hydroxides are potassium and sodium salts. The potassium salts are preferred.

Examples for suitable alkaline earth carbonates and hydroxides are calcium carbonate, calcium hydroxide and barium carbonate. The reaction is conducted at −10° to +70° C., preferably at +25° C.

The introduction of the ester group

for $R_1$ wherein $R_2$ is an alkyl group of 1–10 carbon atoms takes place according to methods known to those skilled in the art. The 1-carboxy compounds are reacted, for example, with diazohydrocarbons in a manner known per se. Esterification with diazohydrocarbons takes place, for example, by mixing a solution of the diazohydrocarbon in an inert solvent, preferably in diethyl ether, with the 1-carboxy compound in the same or in another inert solvent, e.g. methylene chloride. After the reaction has been completed within 1–30 minutes, the solvent is removed and the ester purified as usual. Diazoalkanes are either known or can be prepared according to known methods [Org. Reactions 8:389–394 (1954)].

Introduction of the oxazoline group in the 1-position is conducted according to the process described in DOS 3,115,997.

Introduction of the ester group

for $R_1$ wherein $R_2$ is a substituted or unsubstituted aryl group is conducted according to methods known to persons skilled in the art. For example, the 1-carboxy compounds are reacted with the corresponding arylhydroxy compounds with dicyclohexylcarbodiimide in the presence of a suitable base, e.g. pyridine, DMAP, triethylamine, in an inert solvent. Suitable solvents are methylene chloride, ethylene chloride, chloroform, ethyl acetate, tetrahydrofuran, preferably chloroform. The reaction is performed at temperatures of between −30° and +50° C., preferably at 10° C.

If C=C-double bonds present in the primary product are to be reduced, hydrogenation is effected according to methods known per se.

Hydrogenation of the 5,6-double bond is carried out conventionally at low temperatures, preferably at about −20° C., in a hydrogen atmosphere in the presence of a noble metal catalyst. Suitable as the catalyst is, for example, 10% palladium on carbon.

If the 5,6- as well as 13,14-double bonds are hydrogenated, then the process is conducted at a higher temperature, for example at about 20° C.

The prostaglandin derivatives of general Formula I wherein $R_2$ means a hydrogen atom can be converted under neutralization into a salt with suitable amounts of the corresponding inorganic bases. For example, when dissolving the corresponding PG acids in water containing the stoichiometric quantity of the base, the solid inorganic salt is obtained after evaporation of the water or after addition of a water-miscible solvent, e.g. alcohol or acetone.

For preparation of an amine salt, which is conducted in the usual way, the PG acid is dissolved, for example, in a suitable solvent, e.g. ethanol, acetone, diethyl ether, acetonitrile or benzene, and at least the stoichiometric amount of the amine is added to this solution. During this step the salt is ordinarily obtained in the solid form or is isolated as usual after evaporation of the solvent.

The introduction of the amide group

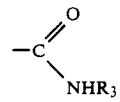

for $R_1$ takes place according to methods known to those skilled in the art. The carboxylic acids of general Formula I ($R_2$=H) are first converted into the mixed anhydride in the presence of a tertiary amine, such as, for example, triethylamine, with isobutyl chloroformate. Reaction of the mixed anhydride with the alkali salt of the corresponding amide or with ammonia ($R_3$=H) takes place in an inert solvent or solvent mixture, e.g. tetrahydrofuran, dimethoxyethane, dimethylformamide, hexamethylphosphoric triamide, at temperatures of between −30° and +60° C., preferably at 0° to 30° C.

Another possibility for introducing the amide group

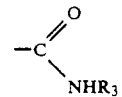

for $R_1$ resides in reacting a 1-carboxylic acid of general Formula I ($R_2$=H) wherein free hydroxy groups are optionally blocked intermediarily, with compounds of general Formula III $$O=C=N-R_3 \qquad (III)$$

wherein $R_3$ has the meanings given above.

Reaction of the compound of general Formula I ($R_2$=H) with an isocyanate of general Formula III likewise takes place with addition of a tertiary amine, such as, for example, triethylamine or pyridine. The reaction can take place without a solvent or in an inert solvent, preferably acetonitrile, tetrahydrofuran, acetone, dimethylacetamide, methylene chloride, diethyl ether, toluene, at temperatures of between −80° and 100° C., preferably at 0°–30° C.

If the starting compound contains OH-groups in the prostane residue, these OH-groups can likewise react so that in these cases starting compounds are suitably employed wherein these are blocked intermediarily by preferably easily cleavable ether or acyl residues.

The compounds of general Formula II serving as the starting material, with a blocked hydroxy group in the 15-position and $R_4$ being free hydroxyl

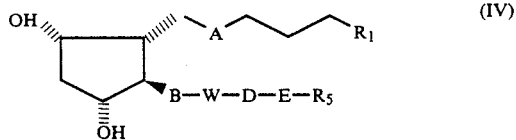

can be prepared, for example, by reacting $9\alpha,11\alpha,15\alpha$-trihydroxyprostanoic acid ester IV with phenylboric acid [T. I. Perun, I. R. Martin and R. S. Egan, J. Org. Chem. 39 : 1490 (1974)] and then selectively acylating the 15-hydroxy group. For W=ethylenedioxy, IV is readily accessible by ketalizing the 15-keto-trans-$\Delta^{13}$ system (cf. DOS 2,434,133).

As compared with $PGD_2$ derivatives, the novel 11-haloprostaglandins are distinguished by higher stability.

The novel 11-haloprostane derivatives of general Formula I are valuable pharmaceuticals since they exhibit, with a similar spectrum of efficacy, a substantially improved (higher specificity) and, above all, substantially longer effectiveness than the corresponding natural prostaglandins.

The active compounds of this invention inhibit gastric acid secretion, show cytoprotective and ulcer-healing effects and thus counteract the undesirable consequences of nonsteroidal anti-inflammatory agents (prostaglandin synthesis inhibitors). They furthermore exhibit cytoprotective activity on the liver and also on the pancreas.

Several of the disclosed compounds possess pronounced antiproliferative properties and, respectively, prevent metastasizing.

Several of the compounds have blood-pressure-lowering effects, regulate disturbances of cardiac rhythm and inhibit platelet aggregation, with the ensuing possibilities for their usage. The novel prostaglandins can also be utilized in combination with, for example, $\beta$-blockers and diuretics.

The novel prostaglandin derivatives are suitable, upon one-time enteral or parenteral administration, for inducing menstruation or terminating pregnancy. They are furthermore suited for synchronizing the sexual cycle in female mammals, such as rabbits, cattle, horses, pigs, etc. Furthermore, the prostaglandin derivatives of this invention are suitable as cervix dilators as a preparation for diagnostic or therapeutic interventions.

The good tissue specificity of the compounds of this invention with antifertility activity is demonstrated in a study on other smooth-muscle organs, such as, for example, on the guinea pig ileum or on the isolated rabbit trachea where a substantially lesser stimulation can be observed than evoked by the natural prostaglandins. The compounds of this invention also act bronchospasmolytically. Besides, they effect shrinkage of the mucous membrane of the nose.

The novel prostaglandin analogs have a strong luteolytic activity, i.e. for triggering luteolysis, substantially lower doses are needed than in case of the corresponding natural prostaglandins.

Also for triggering abortion, especially upon oral or intravaginal administration, substantially lower quantities of the novel prostaglandin analogs are required as compared with the natural prostaglandins.

When recording the isotonic uterus contraction in anesthetized rats and on the isolated rat uterus, it is found that the compounds of this invention are substantially more efficacious, and their effects are of a longer duration, than in case of the natural prostaglandins.

For medical applications, the active agents can be converted into a form suitable for inhaling, for oral, parenteral or local (e.g. vaginal) administration.

Aerosol solutions are suitably prepared for inhalation.

Tablets, dragees or capsules are suitable, for example, for oral administration.

Sterile, injectable aqueous or oily solutions are used for parenteral administration.

Suppositories are suitable and customary, for example, for vaginal administration.

The invention thus also concerns medicinal agents based on the compounds of general Formula I and conventional auxiliary agents and excipients.

The active compounds of this invention are to serve in conjunction with the auxiliary agents known and customary in galenic pharmacy, for example for producing preparations for triggering abortion, for cycle control, for inducing labor, or for the treatment of hypertonia. For this purpose, but also for the remaining applications, the preparations can contain 0.01–50 mg of the active compound.

The following examples are to describe the invention in greater detail without restricting the latter.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding West German Application 33 25 175.4 filed with WIPO on July 8, 1983, are hereby incorporated by reference.

EXAMPLE 1

(5Z,13E)-$9\alpha,15\alpha$-Dihydroxy-$11\beta$-chloro-16,16-dimethyl-5,13-prostadienoic Acid (a) 100 mg (0.25 millimole) of (5Z,13E)-$9\alpha,11\alpha,15\alpha$-trihydroxy-16,16-dimethylprostadienoic acid methyl ester was dissolved in 20 ml of absolute acetonitrile-pyridine (1:1), 0.5 ml of $CCl_4$ was added, and the mixture was cooled to −8° C. Then a solution of 0.262 g (1 mmol) of triphenylphosphine in 10 ml of pyridine-acetonitrile (9:1) was added thereto and the reaction mixture was gradually heated to 24° C. under agitation and then left at 24° C. for 16 hours. After adding 10 ml of toluene, the mixture was evaporated, the residue dissolved in 30 ml of $CH_2Cl_2$ and extracted by shaking with 25 ml of saturated $NaHCO_3$ solution. The aqueous solution was once more extracted with $CH_2Cl_2$. After drying ($Na_2SO_4$) and evaporation, the residue was dissolved in 15 ml of toluene and chromatographed on 100 g of silica gel; by elution with toluene-ethyl acetate (9:1), 54 mg (52%) of 9α,15α-dihydroxy-11β-chloro-16,16-dimethylprostadienoic acid methyl ester was obtained.

(b) 54 mg of the methyl ester was dissolved in 15 ml of methanol and combined at 0° C. with 1 ml of 0.5N KOH solution, then stirred for 72 hours at 23° C., evaporated, combined with $H_2O$ and solid citric acid, and extracted with $CH_2Cl_2$, thus obtaining 45.8 mg (88%) of a light-brown oil of the title compound which was uniform as per thin-layer chromatography.

IR (Film): 615, 950, 1065, 1205, 1360, 1380, 1710, 2920, 2960/cm$^{-1}$

EXAMPLE 2

(5Z,13E)-9α,15α-Dihydroxy-11β-bromo-16,16-dimethyl-5,13-prostadienoic Acid

Analogously to Example 1, 100 mg (0.25 mmol) of (5Z,13E)-9α,11α,15α-trihydroxy-16,16-dimethylprostadienoic acid methyl ester was reacted in absolute acetonitrilepyridine (1:1) with triphenylphosphine and $C_2Br_2Cl_4$; the methyl ester was saponified, yielding the title compound with a total yield of about 30%.

EXAMPLE 3

(5Z,13E)-9α,15α-Dihydroxy-11α-chloro-16,16-dimethyl-5,13-prostadienoic Acid (a) At 24° C., 2.5 g (5 mmol) of (5Z,13E)-9α-benzoyloxy-11α,15α-dihydroxy-16,16-dimethyl-5,13-prostadienoic acid methyl ester in 100 ml of absolute toluene was combined with 6.58 g (25 mmol) of triphenylphosphine and 1.2 g (3 mmol) of zinc tosylate and finally, during a period of 25 minutes, 3.93 ml (25 mmol) of azodicarboxylic acid diethyl ester was added dropwise under agitation. Thereupon the mixture was stirred for one hour at 24° C., 100 ml of $H_2O$ was added, and the mixture was extracted twice with 400 ml of ether, washed with saturated NaCl solution until neutral, and the solution was dried with $M_9SO_4$. After evaporation, the residue was chromatographed with hexane-ether (4:1, then 1:1) on a column of 250 g of silica gel, thus obtaining 1.733 g (53%) of (5Z,13E)-9α-benzoyloxy-11β-tosyloxy-15-hydroxy-16,16-dimethylprostadienoic acid methyl ester.

(b) A solution of 250 mg (0.38 mmol) of the above 11β-tosyloxy compound was heated in 11.3 ml of absolute DMF with 161 mg of dried lithium chloride for 4 hours under argon to 65° C., cooled, and combined with 200 ml of ice-cold saturated NaCl solution After extraction with 400 ml of ether, the mixture was dried ($Na_2SO_4$) and evaporated, and the residue was chromatographed on 100 g of silica gel. Elution with hexa-ether (1:1) yielded 139.3 mg (70.5%) of the desired 11α-chloro compound.

(c) For saponification, 128.8 mg of the above-described compound was stirred with excess KOH in 5 ml of $H_2O/CH_3OH$ for 3 hours at 24° C., evaporated, combined with aqueous citric acid, and extracted with methylene chloride. Chromatography on silica gel with hexane-ethyl acetate produced about 70 mg of the title compound.

IR (Film): 840, 975, 1365, 1385, 1407, 1455, 1710, 2870, 2940, 2960 cm$^{-1}$ (d) The (5Z,13E)-9α,15α-dibenzoyloxy-11α-hydroxy-16,16-dimethyl-5,13-prostadienoic acid methyl ester, described as the starting material for (a), was produced analogously to DOS 3,106,149 by Horner-Wittig reaction of (5E)-9α-benzoyloxy-11α-tetrahydropyran-2-yloxy)-2β-formyl-13,14,15,16, 17,18,19,20-nor-5-prostenoic acid methyl ester with 2-(1,1-dimethylpentyl)-2-oxoethanephosphonic acid dimethyl ester, $NaBH_4$ reduction, 15-epimer separation, and removal of the 11α-tetrahydropyranyloxy blocking group with acetic acid-$H_2O$THF.

EXAMPLE 4

(5Z,13E)-9α,15α-Dihydroxy-11α-bromo-16,16-dimethyl-5,13-prostadienoic Acid

Analogously to Direction 3(b), (5Z,13E)-9α-benzoyloxy-11α-bromo-15α-hydroxy-16,16-dimethylprostadienoic acid methyl ester was prepared by reaction of (5Z,13E)-9α-benzoyloxy-11β-tosyloxy-15α-hydroxy-16,16-dimethylprostadienoic acid methyl ester with anhydrous lithium bromide in absolute DMF.

Gentle saponification with 3–4 equivalents of lithium hydroxide in methanol-$H_2O$ (7 hours, 24° C.), acidification with citric acid and extraction with $CH_2Cl_2$ yielded, after chromatography on silica gel, pure (5Z,13E)-9α,15α-dihydroxy-11α-bromo-16,16-dimethylprostadienoic acid.

EXAMPLE 5

(5Z,13E)-9α,15α-Dihydroxy-11α-fluoro-16,16-dimethyl-5,13-prostadienoic Acid (a) 1.34 g (2.05 mmol) of (5Z,13E)-9α-benzoyloxy-11β-tosyloxy-15α-hydroxy-16,16-dimethyl-5,13-prostadienoic acid methyl ester was dissolved in 75 ml of acetone and combined with 7.36 ml (7.4 mmol) of a solution of absolute tetrabutylammonium fluoride in THF and stirred for 96 hours at 24° C. After the reaction mixture had been worked up, it was chromatographed with hexane-ether (4:1, then 1:1) on 150 g of $SiP_2$, thus isolating 154 mg (15%) of pure (5Z,13E)-9α-benzoyloxy-11α-fluoro-15α-hydroxy-16,16-dimethyl-5,13-prostadienoic acid methyl ester.

(b) Pure (5Z,13E)-9α,15α-dihydroxy-11α-fluoro-6,16-dimethyl-5,13-prostadienoic acid was obtained by saponification of the methyl ester, produced according to Example 5(a), with KOH/methanol/$H_2O$ (4 hours, 24° C.), working up, and chromatography on $SiO_2$ with hexane-ethyl acetate.

EXAMPLE 6

(5Z,13E)-9α-Hydroxy-11β-chloro-15,15-ethylenedioxy-16-phenoxy-17,18,19,20-nor-5,13-prostadienoic Acid Methyl Ester At 24° C., a solution of 1.31 g (5 mmol) of triphenylphosphine in 35 ml of absolute acetonitrile-pyridine (1:1) was added dropwise under agitation during a period of 2 hours to a solution of 0.8939 (2 mmol) of (5Z,13E)-9α,11α-dihydroxy-15,15-ethylenedioxy-16-phenoxy-17,18,19,20-nor-5,13-prostadienoic acid methyl ester [cf. W. Skuballa et al., J. Med. Chem. 21:443 (1978)] and 0.97 ml (10 mmol) of $CCl_4$ in 70 ml of absolute acetonitrile-pyridine (1:1); the mixture was stirred overnight at 24° C. After evaporation while adding toluene, the residue was chromatographed with toluene-ethyl acetate on 60 g of silica gel, thus obtaining 0.53 g (57%) of the title compound.

IR (Film): 690, 755, 950, 980, 1050, 1080, 1174, 1440, 1455, 1495, 1590, 1600, 1735, 2890, 2950 cm$^{-1}$

EXAMPLE 7

(5Z,13E)-9α,15α-Dihydroxy-11β-chloro-16-phenoxy-17,18,19,20-nor-5,13-prostadienoic Acid (a) 400 mg (1 mmol) of (5Z,13E)-9α-11β-chloro-15,15-ethylenedioxy-16-phenoxy-17,18,19,20-nor-5,13-prostadienoic acid methyl ester was stirred with 30 mg of p-toluenesulfonic acid monohydrate in 100 ml of methanol for 24 hours at 24° C.; then once again 30 mg of p-toluene-sulfonic acid hydrate was added and the mixture agitated for 24 hours at 24° C. After evaporation, the residue was shaken with $CH_2Cl_2$ and ice-cold $NaHCO$ solution, reextracted with $CH_2Cl_2$, and the $CH_2Cl_2$ extracts were dried ($Na_2SO_4$) and evaporated, thus obtaining 380 mg of a viscous oil.

After dissolving in 60 ml of methanol, the mixture was reduced by gradual addition of 90 mg of $NaBH_4$ at 0° C. under agitation; finally the mixture was neutralized with a small amount of acetic acid and evaporated. After working up with $CH_2Cl_2$ and ice-cold $NaHCO_3$ solution, 360 mg of crude products was obtained Chromatography on 100 g of $SiO_2$ with toluene-ethyl acetate (9:1) yielded 123 mg of pure 15α-epimer, 89 mg of 15-epimer mixture,.and finally 128 mg of pure 15β-epimer.

(b) Saponification of 65 mg (0.15 mmol) of the α-epimer with 1 ml of 0.5N KOH in 20 ml of methanol (48 hours, 24° C.) produced, after evaporation and working up with citric acid/$CH_2Cl_2$, 35 mg (55.7%) of the title compound.

IR (Film): 695, 760, 975, 1040, 1080, 1175, 1245, 1460, 1500, 1710, 2870, 2930 cm$^{-1}$

EXAMPLE 8

(5Z,13E)-11β-Chloro-9α,15α-dihydroxy-16,19-dimethyl-5,13,18-prostatrienoic Acid

According to the directions given in Example 1, 342 mg of (5Z,13E)-(8R,9S,11R,12R,15S,16RS)-9,15-dibenzoyloxy-11-hydroxy-16,19-dimethyl-5,13,18-prostatrienoic acid methyl ester was reacted for 19 hours at room temperature with 5.63 ml of the mixture described in Example 1, as well as with 298 mg of triphenylphosphine in 3.6 ml of acetonitrile and 0.5 ml of pyridine (period of dropwise addition 1.5 hours). After purification by column chromatography on silica gel with hexane/ethyl acetate (5:1), 323 mg of the 11β-chloro compound was obtained.

IR (Film): 1737, 1720, 1601, 1584, 1491, 1272, 973, 712 cm$^{-1}$

For saponification, 294 mg of the above described 11β-chloro compound was reacted with 4.73 ml of the potassium hydroxide/water/methanol mixture indicated in Example 1 for 22.5 hours at room temperature. After purification by column chromatography on silica gel with ethyl acetate as the mobile phase, 118 mg of the title compound was obtained.

IR (Film): 3400 (broad), 2730, 2650, 1709, 973 cm$^{-1}$

EXAMPLE 9

(5Z,13E)-11β-Fluoro-9α,15α-dihydroxy-16,19-dimethyl-5,13,18-prostatrienoic Acid Methyl Ester A solution of 430 mg of (5Z,13E)-9α,15α-dibenzoyloxy-11α-hydroxy-16,19-dimethyl-5,13,18-prostatrienoic acid methyl ester in 0.7 ml of pyridine was combined at 0° C. under argon with 273 mg of p-toluenesulfonyl chloride and stirred for 13 hours. Then the reaction mixture was combined with 0.4 ml of water, further stirred for 2 hours, diluted with ether, washed with water, twice with respectively 10 ml of cold 5% sulfuric acid, with 10 ml of water, with 10 ml of saturated sodium bicarbonate solution, and once again with water, dried over magnesium sulfate and concentrated to dryness, thus obtaining 514 mg of the 11α-tosylate which was used without further purification in the subsequent stage.

IR (Film): 1737, 1718, 1601, 1584, 1492, 1363, 1273, 1178, 970, 910, 713 cm$^{-1}$ 503 mg of the above-described 11α-tosylate was dissolved in 23.9 ml of acetone and combined dropwise at room temperature under argon with a solution of 2.39 ml of 1-molar tetrabutylammonium fluoride in 5 ml of tetrahydrofuran within 1.75 hours. The mixture was stirred for 42 hours, then the reaction mixture was concentrated on a rotary evaporator, combined with 30 ml of water, and extracted three times with respectively 150 ml of methylene chloride. The combined organic phases were washed with saturated sodium chloride solution, dried over magnesium sulfate and evaporated to dryness. After column chromatography on silica gel with hexane/25–33% ether as the mobile phase, 280 mg of the desired 11β-fluoro compound was obtained in a mixture with the corresponding $\Delta^{11,12}$-compound, of which 221 mg was subjected to saponification according to the directions in Example 2 (20.5 mg of lithium hydroxide, 4.8 ml of water/methanol [1:2], 17.5 hours of reaction time at room temperature). Since, under these reaction conditions, a partial methyl ester cleavage could already be observed, reesterification with ethereal diazomethane solution was required. After separation of the more polar olefin by column chromatography on silica gel with hexane/20% ether as the eluent, 10 mg of the title compound was obtained.

IR (Film): 3400 (broad), 1722, 976 cm$^{-1}$

EXAMPLE 10

(5Z,13E)-11β-Chloro-9α,15α-dihydroxy-16,16,19-trimethyl-5,13,18-prostatrienoic Acid 316 mg of (5Z,13E)-9α,15α-dibenzoyloxy-11α-hydroxy-16,16,19-trimethyl-5,13,18-prostatrienoic acid methyl ester was reacted according to the directions given in Example 1 with 5.1 ml of the mixture described therein, as well as with 269 mg of triphenylphosphine in 3.3 ml of acetonitrile and 0.36 ml of pyridine (period of dropwise addition 2 hours) for 21 hours at room temperature. After purification by column chromatography on silica gel with hexane/ethyl acetate (5:1), 320 mg of the 11β-chloro compound was obtained.

IR (Film): 1735, 1720, 1601, 1584, 1490, 1271, 975, 712 cm$^{-1}$

For saponification, 305 mg of the above-described 11β-chloro compound was reacted with 9.6 ml of the potassium hydroxide/water/methanol mixture indicated in Example 1 for 28.5 hours at room temperature. After purification by column chromatography on silica gel with hexane/50–100% ethyl acetate as the eluent, 91 mg of the title compound was obtained.

IR (Film): 3420 (broad), 2730, 2660, 1709, 976 cm$^{-1}$

EXAMPLE 11

(5Z, 13E)-9alpha,15alpha-dihydroxy-11alpha-fluoro-15-cyclohexyl-16,17,18,19,20-pentanor-5,13-prostadienoic acid (a) 32.9 mg (0.054 m mol) of (5Z,13E)-11beta-hydroxy-9alpha,15alpha-dimethyl-tert-butyl-silyloxy-16,17,18,19,20-pentanor-5,13-prostadienoic acid methyl ester was dissolved in 1.9 ml of toluene and mixed under argon with 0.019 ml of pyridine and 0.022 ml of diethylaminosulfur trifluoride (DAST) at −70° and stirred for 45 minutes with the temperature being maintained.

After working up by mixing of the reaction mixture with 2.1 ml of 5% NaHCO$_3$ solution, 15 minutes stirring, extraction with 300 ml of ether, neutral washing of the organic phase with 20 ml of saturated NaCl solution, drying over MgSO$_4$ and concentration by evaporation, 8.88 mg (26.9% of theory) is obtained.

(b) After cleavage of the silyl protection group with acetic acid/water/tetrahydrofuran (65/35/10), the purified 9alpha,15alpha-dihydroxy-5,13-prostadienoic acid methyl ester (22.92 mg) is stirred with 2.4 ml of a mixture of KOH/methanol/water (3.6 g/120 ml/24 ml) for 18 hours at room temperature. After working up and chromatography on SiO$_2$ with hexane/acetic acid, 12.7 mg of the title compound is obtained.

IR (film): 3400 (broad), 2410, 1708, 970/ cm.

EXAMPLE 12

(5Z,13E)-9alpha,15alpha-dihydroxy-11alpha-chloro-15-cyclohexyl-16,17,18,19,20-pentanor-5,13-prostadienoic acid The corresponding 11alpha-chloro compound was obtained by 4-hour heating of (5Z,13E)-9alpha,15alpha-dibenzoyloxy-11betatosyloxy-15-cyclohexyl-16,17,18,19,20-pentanor-5,13-prostadienoic acid methyl ester with anhydrous lithium chloride in absolute DMF and under argon. Working up took place by mixing with ice-cold saturated NaCl solution, extraction with ether, drying on Na$_2$SO$_4$, concentration by evaporation, chromatography on silica gel, elution with hexane/ether (1:1).

Careful saponification with 3–4 equivalents of KOH in methanol-water (21 hours at room temperature), acidification with 10% citric acid to pH 5, extraction with acetic acid yielded, after chromatography on silica gel, 65% of pure title compound.

What is claimed is:

1. An 11-chloro- or 11-fluoroprostane derivative of the formula (I)

wherein
X is F or Cl,
R$_1$ is CH$_2$OH,

R$_2$ is (a) H; (b) C$_{1-10}$ alkyl; (c) C$_{1-10}$ alkyl substituted by halogen, C$_{1-4}$ alkoxy, C$_{6-10}$ aryl, C$_{6-10}$ aroyl, C$_{6-10}$ aryl, or C$_{6-10}$ aroyl each substituted as defined below, dialkylamino or trialkylammonium; (d) phenacyl; (e) C$_{6-10}$ aryl or C$_{6-10}$ aryl substituted by 1–3 halogen atoms, phenyl, 1–3 C$_{1-4}$-alkyl groups, chloromethyl, fluoromethyl, trifluoromethyl, carboxy, hydroxy, or C$_{1-4}$ alkoxy; (f) C$_{3-10}$ cycloalkyl or C$_{3-10}$ cycloalkyl substituted by C$_{1-4}$ alkyl; or (g) 5- or 6-membered aromatic heterocyclic ring containing an N, O, or S atom;

R$_3$ is an acyl group of a C$_{1-15}$ hydrocarbon carboxylic or sulfonic acid, or a group defined for R$_2$;

R$_4$ is OR;

R is H, an acyl group of a C$_{1-15}$ hydrocarbon carboxylic or sulfonic acid, tetrahydropyranyl, tetrahydrofuranyl, alpha-ethoxyethyl, trimethylsilyl, dimethylsilyl, tert-butylsilyl, or tribenzylsilyl;

R$_5$ is C$_{3-10}$ cycloalkyl or C$_{3-10}$ cycloalkyl substituted by C$_{1-4}$ alkyl;

R$_8$ is C$_{1-5}$ alkyl;

R$_9$ is H or methyl;

A is —CH$_2$—CH$_2$— or cis—CH=CH—;

B is —CH$_2$—CH$_2$—, trans—CH=CH— or —C≡C—;

W is ethylenedioxymethylene or —CH$_2$OR, wherein R is as defined above;

Y is a single bond; C$_{1-5}$ alkylene or C$_{1-5}$ alkylene substituted by C$_{1-4}$ alkyl;

D and E jointly represent a single bond or

D is C$_{1-10}$ alkylene or C$_{1-10}$ alkylene substituted by fluorine, C$_{2-10}$-alkenylene or C$_{2-10}$-alkenylene substituted by fluorine;

E is O, S, a single bond, a —C≡C— bond or —CR$_6$=CR$_7$, wherein R$_6$ and R$_7$ are different from a physiologically acceptable salt thereof.

2. A compound of claim 1, wherein X is Cl.
3. A compound of claim 1, wherein X is F.
4. A compound of claim 1, wherein R$_1$ is R$_2$ is H, A is cis—CH=CH—, R$_4$ is —OR, R is H, B is trans—CH=CH—, and W is CH$_2$OR.

5. A compound of claim 4, wherein X is Cl.
6. A compound of claim 4, wherein X is F.
7. A compound according to claim 1, wherein R$_5$ is cyclohexyl.
8. A compound of claim 7, wherein R$_1$ is R$_2$ is H, A is cis—CH=CH—, R$_4$ is —OR, R is H, B is trans—CH=CH—, and W is CH$_2$OR.

9. A compound of claim 7, wherein X is Cl.
10. A compound of claim 7, wherein X is F.
11. (5Z,13E)-9α,15α-dihydroxy-11α-fluoro-15-cyclohexyl-16,17,18,19,20-pentanor-5,13-prostadienoic acid.
12. (5Z,13E)-9α,15α-dihydroxy-11α-chloro-15-cyclohexyl-16,17,18,19,20-pentanor-5,13-prostadienoic acid.

13. A pharmaceutical composition comprising an effective amount of a compound of claim 1 and a pharmaceutically acceptable carrier.

14. A pharmaceutical composition comprising an effective amount of a compound of claim 11 and a pharmaceutically acceptable carrier.

15. A pharmaceutical composition comprising an effective amount of a compound of claim 12 and a pharmaceutically acceptable carrier.

* * * * *